(12) United States Patent
Karimzadeh et al.

(10) Patent No.: US 10,021,087 B2
(45) Date of Patent: Jul. 10, 2018

(54) METHOD AND SYSTEM FOR PROVIDING A SECURE COMMUNICATION CHANNEL TO PORTABLE PRIVATIZED DATA

(71) Applicants: Mansour Aaron Karimzadeh, Great Neck, NY (US); F. Avraham Dilmanian, Yaphank, NY (US); Farshad Namdar, Forest Hills, NY (US)

(72) Inventors: Mansour Aaron Karimzadeh, Great Neck, NY (US); F. Avraham Dilmanian, Yaphank, NY (US); Farshad Namdar, Forest Hills, NY (US)

( * ) Notice: Subject to any disclaimer, the term of this patent is extended or adjusted under 35 U.S.C. 154(b) by 260 days.

(21) Appl. No.: 14/837,144

(22) Filed: Aug. 27, 2015

(65) Prior Publication Data
US 2016/0080364 A1 Mar. 17, 2016

Related U.S. Application Data

(60) Provisional application No. 62/050,291, filed on Sep. 15, 2014, provisional application No. 62/105,813, filed on Jan. 21, 2015.

(51) Int. Cl.
*H04L 29/06* (2006.01)
*H04W 12/06* (2009.01)
(Continued)

(52) U.S. Cl.
CPC ......... *H04L 63/0823* (2013.01); *G06F 21/34* (2013.01); *G06F 21/606* (2013.01);
(Continued)

(58) Field of Classification Search
CPC ...... G06F 19/322–19/323; G06F 21/31; G06F 21/33–21/35; G06F 21/44–21/445;
(Continued)

(56) References Cited

U.S. PATENT DOCUMENTS 7,661,146 B2 * 2/2010 Karimzadeh ......... G06F 21/604
726/27
2011/0010539 A1 * 1/2011 Salomone ............... H04L 9/321
713/155

(Continued)

OTHER PUBLICATIONS

Bluetooth Specification Version 4.0 [vol. 0]. Publication date: Jun. 30, 2010. (Year: 2010).*

*Primary Examiner* — Kevin Bechtel
(74) *Attorney, Agent, or Firm* — Betsy Kingsbury Dowd; BKDowd Law, P.C.

(57) ABSTRACT

A system and method for communicating secure, privatized data stored on a first user device with a second user device requesting access thereto includes initiating a timed access gate for receiving verification of authenticating credentials from the second user device, after the first user credentials associated with the first user device are verified. If the second user device is verified within the predetermined period of time, an authentication handshake between the first user device and the second user device is completed. On completion of the handshake, a communication channel is opened for transmitting the first user's privatized data between the first user device and the second user device.

23 Claims, 5 Drawing Sheets

(51) Int. Cl.
*G06F 21/60* (2013.01)
*G06F 21/62* (2013.01)
*G06F 21/34* (2013.01)
*G16H 10/60* (2018.01)
*H04W 12/08* (2009.01)
*H04W 4/80* (2018.01)

(52) U.S. Cl.
CPC ......... *G06F 21/6245* (2013.01); *G16H 10/60* (2018.01); *H04L 63/102* (2013.01); *H04W 12/06* (2013.01); *H04W 4/80* (2018.02); *H04W 12/08* (2013.01)

(58) Field of Classification Search
CPC ........ G06F 21/60–21/606; G06F 21/62; G06F 21/6245; G06Q 20/40–20/40975; G06Q 50/22–50/24; H04L 63/08; H04L 63/0823–63/0853; H04L 63/0869–63/0892; H04L 63/102; H04L 63/105; H04L 63/108; H04W 4/008; H04W 12/02; H04W 12/06; H04W 12/08
See application file for complete search history.

(56) References Cited

U.S. PATENT DOCUMENTS

| | | | |
|---|---|---|---|
| 2014/0056313 A1* | 2/2014 | Wada | H04L 63/02 370/463 |
| 2014/0207686 A1* | 7/2014 | Experton | G06F 19/3418 705/51 |
| 2015/0096001 A1* | 4/2015 | Morikuni | H04L 63/08 726/7 |

* cited by examiner

METHOD AND SYSTEM FOR PROVIDING A SECURE COMMUNICATION CHANNEL TO PORTABLE PRIVATIZED DATA

CROSS-REFERENCE TO RELATED APPLICATIONS

This application claims the benefit of and priority to U.S. Provisional Application Ser. No. 62/050,291, entitled "METHOD AND SYSTEM FOR PROVIDING A SECURE MULTI-USER PORTABLE DATABASE," filed Sep. 15, 2014, and U.S. Provisional Application Ser. No. 62/105,813, entitled "METHOD AND SYSTEM FOR PROVIDING A SECURE MULTI-USER PORTABLE DATABASE," filed Jan. 21, 2015, the entirety of each of which is hereby incorporated herein by reference thereto.

FIELD OF THE DISCLOSURE

The present disclosure relates generally to a secure, multi-user portable database and, more particularly, to a system and method for providing a secure communication channel between a portable database having privatized data stored therein and a device requesting access thereto.

BACKGROUND

Conventionally, portable storage of data has been commercially available for electronically storing text, such as addresses and phone numbers, or for simple storage and access of a common type of digital media, such as music. These databases, commonly provided on flash memory cards or Universal Serial Bus (USB) tokens have nominal or no built-in security, since the intended use is for non-sensitive data storage and access for a single user. In other words, these products do not provide for the portable storage of secure, privatized data, and a means for multiple parties to access such protected data in a controlled way. There is a need for a portable, multi-user, secure database and a system and method for storage and retrieval of select data by an authorized user.

In particular, there is a need in the current fragmented health care system in the United States and in other countries for a generic database and network for the exchange of patient health information among different health-care providers. The U.S. health care system is made up of many entities spread over a large geographic area, with minimal or no communications or coordination among them for exchange of patient health data. Information is generally owned and kept by the health care provider generating the data, and will only be copied to another if expressly asked for. As a result, physicians do not have easy routine access to the patient's general medical records except for what they themselves produce. In addition, patients going from one health care provider to another usually do not have the relevant records and test results with them. This system results in a number of major problems including delays in diagnosis and treatment, inefficient use of time and resources, unnecessary repetition of tests, and errors in medical practices that could lead to thousands of deaths each year.

Finally, the physician's lack of immediate access to patient information also encourages fraud and abuse of our current health care system. The consequences of such abuse, which may include unnecessary and repetitive tests, for example, are increased insurance premiums, and, therefore, increased cost to the consumer. There is clearly a need, therefore, for a more accessible, portable, and efficient system for exchanging patient health information among different health-care providers.

There is also a need for a system and method of managing and accessing medical data that maintains a patient's privacy. In fact, as a result of the Health Insurance Portability and Accountability Act (HIPAA) enacted by Congress in 1996, U.S. health care providers are now mandated to maintain patient data in a private and secure manner. In accordance with HIPAA, patient health care information can only be divulged by a physician to other health care providers upon the consent of the patient.

Though some attempts have been made to implement an accessible electronic medical information system, none of them provide the accessibility, security, and portability needed to address the current problems in our health care system. U.S. Pat. No. 5,899,998 to McGauley et al., for example, discloses a method and system for maintaining and updating computerized medical records. The system includes a set of databases that propagate data from one database to the other over a network. Encryption techniques are used to maintain the security of the data only when it is being transmitted to other computers.

Similarly, U.S. Pat. No. 6,463,417 to Schoenberg discloses a method and system to allow access to patient data over a communications network. All patient medical records are stored on a number of computers. Access to these computers is only available via a communications network. Should the network fail, the access to the data will be lost. In addition, access to such a host-based database requires access to another provider's system or another insurance company's database, which may not be easily accessible due to business reasons.

U.S. Pat. No. 6,523,116 to Berman discloses a personal card that contains a public key to access a centralized database. The public key identifies the patient, whose medical record is needed, and allows access to the data. The card only provides the user access to the database. No medical data records are available on the card. The user needs either direct access or an access point that is connected to the computer that hosts the centralized database, generally through a network.

U.S. Pat. No. 5,832,488, to Eberhardt discloses storage of a patient's medical history on a smart card. The medical history on the card can be updated, and also stored on a computer database. The card is associated with an ID number, rather than a name, and only health care providers have a list to associate the ID number with a name. The data is not otherwise protected or secure, and there is no mechanism for a patient to selectively authorize a physician access to particular data records saved on the card. In summary, none of these systems provide a database that is portable and easily accessible to both health care providers and patients within an environment that adequately protects the patient's privacy.

These and other prior art systems and methods for providing a medical database, which include server-based storage, low-tech compact disc (CD) formats, or low-memory smart cards, have at least the following limitations. The server-based solutions do not allow off-line access to the data, the low-memory smart cards have very limited storage capability and are generally used only as identification tokens, and CDs are neither easy to use nor flexible enough to handle the necessary security requirements. Other limitations of the prior art include: the inability to provide integrated data across multiple providers; the inability to provide the patient (and the doctor) easy access to the patient's own medical data and medical history; and the lack of a standard format where the data can be easily stored in a secure form and "mined."

Co-owned U.S. Pat. No. 7,661,146 to Karimzadeh, et al., entitled "A Method and System for Providing a Secure Multi-User Portable Database," issued Feb. 9, 2010, discloses a secure multi-user portable database, e.g., on a smart card or on a smart phone or on another similar device, to allow the healthcare providers to store patient medical data securely on the device and to allow the patient to have viewing access to the data on it. The '146 patent discloses an authentication process between the patient card and the healthcare provider card, which includes both the patient and the doctor entering his or her ID and password into separate card readers and keeping both cards inserted in the card readers until the patient's card is read and updated by the healthcare provider. Accordingly, this authentication method relies on a pair of expensive card readers. In addition, there is no decoupling of the communication process for communicating (e.g., reading, writing and updating) the patient's data from the authentication process, both requiring the presence of both the doctor's and patient's cards in their respective card readers.

There is still a need, therefore, for a system and method for providing a secure communication channel, and hierarchical multi-user access to, secure data stored on a portable database.

SUMMARY

Features of the disclosure will become apparent from the following detailed description considered in conjunction with the accompanying drawings. It is to be understood, however, that the drawings are designed as an illustration only and not as a definition of the limits of this disclosure.

The present disclosure provides a system and method for a handshake process for authentication between a first user device associated with a first user, for example, a patient, and a second user device, associated with a second user, for example, a physician, requesting access to a portable database stored on the first user device. The portable database includes privatized, secure data associated with the first user. The handshake process may be decoupled from a communication channel over which the data is transmitted between the portable database and the second user device. Privatized, secure data associated with the first user is stored in the portable database, and, in some aspects, is encrypted for secure hierarchical multi-user access. Authentication of the second user device, which is associated with a second user, may be coupled to a hierarchical level of authorization assigned to the second user. The assignment of hierarchical levels of authorization to users provides secure multi-user access to the portable database. This can be achieved by encrypting a digital certificate, for example, with the hierarchical level of authorization.

In aspects, the handshake process for authentication includes receiving and verifying authenticating credentials from a first user device and a second user device within a predetermined length of time, thereby completing an authentication process. The method further includes opening a communication channel for allowing the second device access to the secure, privatized data in the portable database in response to the authentication process being successfully completed within the predetermined length of time.

One method of the present disclosure for communicating secure, privatized data between a first user device and a second user device of the present disclosure includes receiving, by a processing device, authenticating credentials associated with a first user from a first user device, and verifying, by the processing device, the authenticating credentials associated with the first user. The method further includes initiating a timer, by the processing device, and opening an access gate for a predetermined period of time in response to receiving verification of the authenticating credentials from the first user device. The access gate allows receipt and verification of authenticating credentials from a second user device within the predetermined period of time.

The afore-mentioned steps may be performed, in embodiments, on the first user's device (for example, a smart card, mobile phone and so on) independently of any reader or other device.

The method further includes opening, by the processing device, a communication channel for transmitting secure, privatized data associated with the first user between the first user device and the second user device in response to receiving verification of the authenticating credentials from the second user device within the predetermined period of time.

In aspects, the first user device transmits an "open gate" message to a reading device, which, in various embodiments, may be a card reader, a barcode reader, a wireless reader, and so on, with the initiation of the timer, in response to verifying the first user's authenticating credentials.

In aspects, the method further includes establishing a connection between the first user device and the second user device, and receiving, by the processing device, the verification from the second user device via the connection.

In further aspects, the first user device is one of a mobile device and a smart card, the secure, privatized data being stored in a storage component on the first user device.

The storage component may include both a secure portion for storing security elements and a non-secure portion for storing encrypted data, including the secure privatized data and encrypted security elements.

In some aspects, the first user device may include a keypad, the authenticating credentials associated with the first user being received via the keypad.

The method may further include transmitting information from the first user device to the second user device in response to opening the access gate, the information including a request for the verification of the authenticating credentials associated with the second user from the second user device.

The privatized data may include, in some aspects, medical records associated with the first user. The information may include an identifier associated with the patient and a verification of the authenticating credentials associated with the first user.

In aspects, the first user device is a mobile device with an app installed thereon, and the method may further include receiving and verifying the authenticating credentials associated with the first user and establishing the connection via the app.

In additional aspects, the first user device is a near-field communication enabled device, the connection is a near-field communication connection between the first user device and the second user device. The method further includes transmitting the information in response to establishing the near-field communication connection between the first user device and the second user device, such as when the first user device is positioned in sufficient proximity to the second user device for establishing the connection.

In further aspects, the authenticating credentials associated with the second user include a key and a digital certificate stored on the second user device. The digital certificate may be encrypted with a predetermined authorized level of access granted to the second user for accessing the secure, privatized data. The method, in embodiments, further includes granting the second user access to the secure, privatized data in accordance with the predetermined level of access.

Additional aspects of the method include the second user device re-authenticating itself at a predetermined fixed interval via the connection to maintain the communication channel open between the first user device and the second user device for continued access by the second user device to the secure, privatized data.

Further aspects may include storing the secure, privatized data on the first user device, and, after the step of opening the communication channel, updating the secure, privatized data based on data received from the second user device.

In aspects, the method further includes placing an indicator on the first user device in response to receiving the verification of the second user device and establishing the connection. The connection may then be interrupted, and upon reconnection, the secure, privatized data may still be updated on the first user device via the communication channel within a preset time interval after the interruption without requiring re-verification of the second user device. The updating, after the interruption, further includes detecting the indicator on the first user device.

In some aspects, the first user device is a smart card, and the connection is established via a smart card reader operably connected to the second user device upon connecting the smart card to the smart card reader within the predetermined period of time. The smart card may receive and verify the first user's authenticating credentials entered on the smart card by the first user prior to establishing the connection. The method further includes, in aspects, transmitting the secure, privatized data over the communication channel via the smart card reader.

The smart card, in aspects, may be near-field communication enabled, and the smart card reader a near-field communication device, the two communicating via a near-field communication connection.

In some aspects, the connection between the first user device and the second user device is one of an NFC-enabled connection and a wireless connection.

In various aspects of the present disclosure, the second user device (device requesting access) may be any device that includes a processing device, and memory, including computer readable memory, that is accessible by the processing device for storing instructions that when executed by the processing device causes the processor to implement the steps of the methods described herein.

In various additional aspects, the first user device may be any portable device that can be configured to allow a secure and limited-time open access handshake between the portable device and the device requesting access, and includes a processing device, a storage device for storing the secure data, and memory including computer readable memory accessible by the processing device for storing instructions that when executed by the processing device causes the processor to implement the steps of the methods described herein including allowing read and write access to the data stored in the storage device.

In some aspects, the storage device includes both a secure portion for storing security elements and a non-secure portion for storing encrypted data, including the secure privatized data and encrypted security elements.

In aspects, the method may further include receiving, by the processing device, a request to view the secure, privatized data in response to opening the access gate, and displaying the secure, privatized data via a graphical user interface operably connected to the first user device.

Further aspects may include receiving, by the processing device, a request from the first user device to view and modify settings on the first user device, displaying a menu of allowable actions via a graphical user interface operably connected to the server in response to the request, and storing changes while the access gate is open.

In some aspects, the authenticating credentials of both the first user and the second user are transmitted to an authentication server for verifying the credentials of both. The verification is transmitted back to the first user device and access to the secure, privatized data is granted to the second user device in response to receiving verification of the credentials of both the first user and the second user.

The present disclosure is also directed to a method for communicating secure, privatized data between a first user device associated with a first user, and a second user device. The method includes: receiving, by a server, authenticating credentials and an identifier associated with a first user from a first user device. The server verifies the authenticating credentials associated with the first user and transmits information associated with the first user to a second user device. The information includes a verification of the authenticating credentials of the first user and a request for verification of authenticating credentials associated with a second user from the second user device. The method further includes initiating a timer, by the server, and opening an access gate for a predetermined period of time in response to verifying the authenticating credentials from the first user device. The access gate allows receipt, by the server, of verification of authenticating credentials associated with the second user from the second user device within the predetermined period of time. The server opens a communication channel between the first user device and the second user device for transmitting secure, privatized data associated with the first user in response to the server receiving verification of the authenticating credentials from the second user device within the predetermined period of time.

The first user device, the second user device, and the server may communicate, in embodiments, via a wireless network.

In aspects, the authenticating credentials associated with the second user include a key and a digital certificate stored on the second user device. The digital certificate is encrypted with a predetermined authorized level of access granted to the second user. The method further includes granting the second user access to the secure, privatized data in accordance with the predetermined level of access.

Another method of the present disclosure for communicating secure, privatized data between a first user device associated with a first user, and a second user device includes receiving, by a server, authenticating credentials associated with a first user from the first user device via an app on the first user device, wherein the first user device is a mobile device. The server verifies the authenticating credentials and generates a verification associated with the first user. The server then transmits the verification of the first user to the first user device, and transmits a request for information associated with the first user and for verification of its authenticating credentials to the second user device.

The method further includes initiating a timer, by the server, and opening an access gate for a predetermined period of time in response to transmitting the requests to the second user device. The access gate allows receipt, by the server, of the verification of authenticating credentials associated with the second user, and of the information requested, from the second user device within the predetermined period of time. The server opens a communication channel for transmitting secure, privatized data associated with the first user between the first user device and the second user device in response to the server receiving the information and the verification of the authenticating credentials from the second user device within the predetermined period of time.

In aspects, the information received by the server is derived from a barcode that is scanned by the second user device within a predefined interval of time after being generated. The barcode scanned by the second user device is generated by the first user device via the app upon receiving the verification from the server. The barcoded information includes an identifier associated with the first user and a time and date the information is scanned.

In aspects, the authenticating credentials associated with the second user include a key and a digital certificate stored on the second user device. The digital certificate is encrypted with a predetermined authorized level of access granted to the second user. The method further includes granting the second user access to the secure, privatized data in accordance with the predetermined level of access.

Aspects of the method may further include receiving, by the server, a request from the first user device to view the secure, privatized data, in response to opening the access gate, and displaying the secure, privatized data via a graphical user interface operably connected to the server.

Additional aspects may include receiving, by the server, a request to view and modify settings on the first user device, displaying a menu of allowable actions via a graphical user interface operably connected to the server in response to the request, and storing changes, by the server, while the access gate is open.

In addition to the above aspects of the present disclosure, additional aspects, objects, features and advantages will be apparent from the embodiments presented in the following description and in connection with the accompanying drawings.

BRIEF DESCRIPTION OF THE DRAWINGS

The drawings constitute a part of this disclosure and include examples, which may be implemented in various forms. It is to be understood that in some instances, various aspects of the disclosure may be shown exaggerated or enlarged to facilitate understanding. The teaching of the disclosure can be readily understood by considering the following detailed description in conjunction with the accompanying drawings.

DETAILED DESCRIPTION

Figure 1:
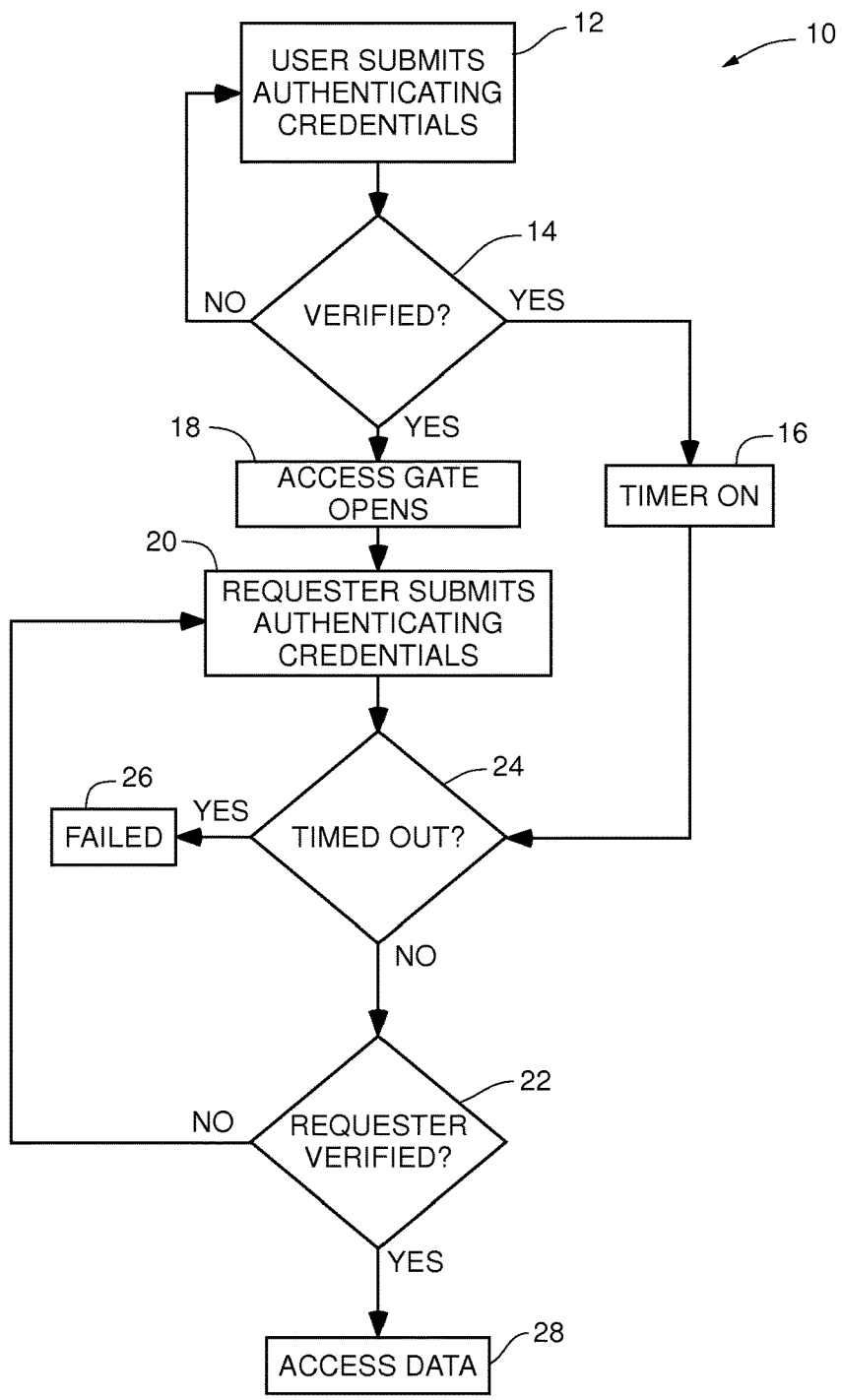
FIG. 1 is a flow diagram representation of an embodiment of a method of the present disclosure.

The following sections describe particular embodiments. It should be apparent to those skilled in the art that the described embodiments provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present method and system as defined herein and equivalents thereto.

Throughout the description, where items are described as having, including, or comprising one or more specific components, or where methods are described as having, including, or comprising one or more specific steps, it is contemplated that, additionally, there are items of the present disclosure that consist essentially of, or consist of, the one or more recited components, and that there are methods according to the present disclosure that consist essentially of, or consist of, the one or more recited processing steps.

It should also be understood that the order of steps or order for performing certain actions is immaterial, as long as the method remains operable. Moreover, two or more steps or actions may be conducted simultaneously or concurrently.

Furthermore, various embodiments may be described herein in terms of functional block components, code listings, optional selections, page displays, and various processing steps. It should be appreciated that such functional blocks may be realized by any number of hardware and/or software components configured to perform the specified functions. For example, the present disclosure may employ various integrated circuit components, e.g., memory elements, processing elements, logic elements, look-up tables, and the like, which may carry out a variety of functions under the control of one or more microprocessors or other control devices.

Similarly, the software elements of the present disclosure may be implemented with any programming or scripting language such as C, C++, C#, Java, COBOL, assembler, PERL, Python, PHP, or the like, with the various algorithms being implemented with any combination of data structures, objects, processes, routines or other programming elements.

The object code created may be executed by any device having a data connection capable of connecting to the Internet, on a variety of operating systems including without limitation Apple OSX®, Apple iOS®, Google Android®, HP WebOS®, Linux, UNIX®, Microsoft Windows®, and/or Microsoft Windows Mobile®.

It should be appreciated that the particular embodiments described herein are illustrative of the disclosure and its best mode, if known, and are not intended to otherwise limit the scope of the present disclosure in any way. Examples are presented herein which may include sample data items which are intended as examples and are not to be construed as limiting. For the sake of brevity, conventional data networking, application development and other functional aspects of the systems (and components of the individual operating components of the systems) may not be described in detail herein.

As should be appreciated by one of ordinary skill in the art, many alternative or additional functional relationships or physical or virtual connections may be present in a practical electronic system or apparatus. In the discussion contained herein, the terms user interface element, button, and tab, are understood to be non-limiting, and include other user interface elements such as, without limitation, a hyperlink, clickable image, and the like.

The present disclosure may be embodied as a method, a data processing system, a device for data processing, or a computer program product. The methods and method steps may be implemented via a computer program installed on a computer system, for example on the health provider's computer system, or on a third-party server device, on a smart card or other mobile device, and/or via a programming application (sometimes referred to as an "app") installed on a mobile device such as a smart phone, tablet, wearable smart device or other such device, or a service, e.g., a programming application installed on a server system and hosted on a server device, which is accessible, for example, via a website from a computer or smart device. In certain embodiments, the programming steps for performing the methods formed in accordance with the present disclosure may be distributed between more than one system and/or device. The computer systems and devices (e.g., smart card, mobile devices, and so on) formed in accordance with the present disclosure include a processing device, and memory for storing the processing steps that when executed by the processing device perform the method steps described herein.

In various embodiments, the present disclosure may take the form of an entirely software embodiment, an entirely hardware embodiment, or an embodiment combining aspects of both software and hardware. Furthermore, the present disclosure may take the form of a computer program product on a computer-readable storage medium having computer-readable program code means embodied in the storage medium. Any suitable computer-readable storage medium may be utilized, including hard disks, CD-ROM, DVD-ROM, optical storage devices, magnetic storage devices, portable memory or storage devices, including semiconductor devices, flash memory, USB thumb drives, SIM cards, and other portable memory chips, and/or the like. Preferably, suitable memory and storage media include a secure storage area or element which can store security components, such as encryption/decryption keys, certificates, and so on, as well as non-secure area, which can store encrypted data (medical) records as well as encrypted keys, encrypted certificates and the like.

Computer program instructions embodying the present disclosure may also be stored in a computer-readable memory that can direct a computer or other programmable data processing apparatus to function in a particular manner, such that the instructions stored in the computer-readable memory produce an article of manufacture, including instruction means, that implement the function specified in the description and/or flowchart block(s). The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the present disclosure.

One skilled in the art will also appreciate that any databases, systems, or components of the present disclosure may consist of any combination of databases or components at a single location or at multiple locations. Furthermore, each database or system includes any of various suitable security features, such as firewalls, access codes, encryption, de-encryption, compression, decompression, and/or the like.

The disclosed systems and/or methods may be embodied, at least in part, in application software that may be downloaded, in whole or in part, from either a website or an application store ("app store") to the mobile device. In another embodiment, the disclosed system and method may be included in the mobile device firmware, hardware, and/or software.

An "app" is used herein as that term is known, to refer to a software application designed to run on a mobile device, such as a mobile or smart phone, tablet, wearable smart device, or any other such mobile device known in the art.

A wireless network as referred to herein broadly refers to any combination of wireless connections including, but not limited to, cellular, WiFi, local area networks, wide area networks, and personal area networks.

In yet other embodiments, all or part of the disclosed systems and/or methods and/or steps may be provided as one or more callable modules, an application programming interface (e.g., an API), a source library, an object library, a plug-in or snap-in, a dynamic link library (e.g., DLL), or any software architecture capable of providing the functionality disclosed herein.

Co-owned U.S. Pat. No. 7,661,146 to Karimzadeh, et al., entitled "A Method and System for Providing a Secure Multi-User Portable Database," issued Feb. 9, 2010, the entirety of which is incorporated herein by reference, discloses a secure multi-user portable database, e.g., on a smart card or on a smart phone or other similar devices, to allow the healthcare providers to store patient medical data securely on the device and to allow the patient to have viewing access to the data on it. The '146 patent discloses a hierarchical level of access which is encrypted into the digital certificate of a user. This allows secure multi-user access to the portable database, as described therein. The '146 patent discloses an authentication process between the patient card and the healthcare provider system, which requires both the patient and the doctor entering his or her ID and password into separate card readers. Both cards remain inserted in the card readers while the patient's card is read and updated by the healthcare provider. There is no decoupling of the communication process for communicating (e.g., reading, writing and updating) the patient's data from the authentication process, both requiring the presence of both the doctor's and patient's cards in their respective card readers.

The system and methods of the present disclosure include improvements to the secure multi-user portable database disclosed in the '146 patent, the entirety of which is incorporated herein by reference. For example, the present system and methods provide a timed access gate for a user (patient, for example) and a requester (physician, for example) requesting access to verify their credentials before allowing communication between the user's portable database and the requester device. This allows certain advantages, such as allowing the authentication process to be decoupled from the communication process. In various embodiments, the credentials can be re-authenticated on a periodic basis during the time the channel of communication remains available for accessing the portable database.

It should be understood that while the embodiments are described herein primarily for the example of a physician accessing a patient's data from a secure smart device formed in accordance with the present disclosure during a doctor's visit, the disclosure is not limited thereto, nor is it limited to privatized medical data. On the contrary, the methods of the present disclosure can be implemented for secure access of any type of data.

Referring to FIG. 1, one embodiment of a method 10 formed in accordance with the present disclosure for authorizing communication between a first device associated with a first user, and a second device associated with a second user, includes the first user device receiving the first user's authenticating credentials 12. For example, the first user device may be a smart card 30 shown in FIG. 2, through which the first user/patient enters his or her authenticating credentials, such as a PIN. Secure data associated with the first user, e.g., a patient, is stored in a portable database on the first device. The smart card may have a secure storage portion or chip for data and security tokens, and a processor configured to securely store the cardholder's PIN and verify the PIN entered by the cardholder, when entered for authentication. If the authenticating credentials for the first user are verified 14, a timer is started 16 and an access gate opens 18.

In various embodiments, the authentication process additionally, or alternatively, includes biometric authentication of the first user, in accordance with methods well known in the art.

Figure 2:
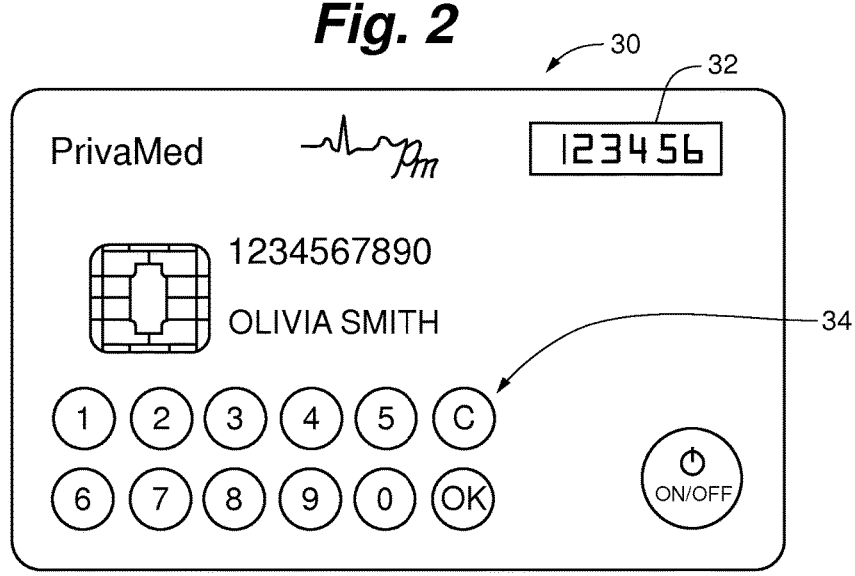
FIG. 2 is a pictorial representation of an embodiment of a user device for storing secure, privatized data in a portable database associated with the user.
Figure 3C:
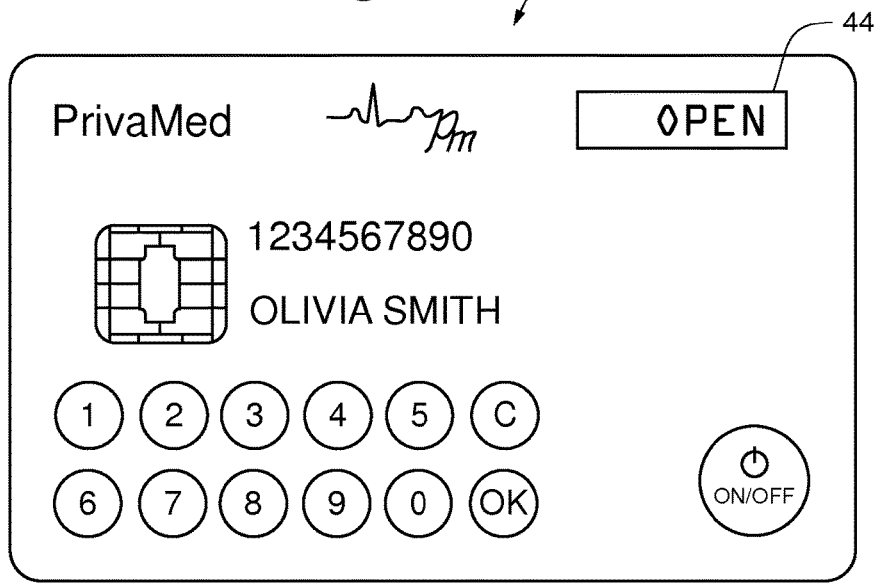
FIG. 3C is a pictorial representation of the embodiment of a user device shown in FIG. 2, shown with the display window that displays another current status of the authentication process.
Figure 4A:
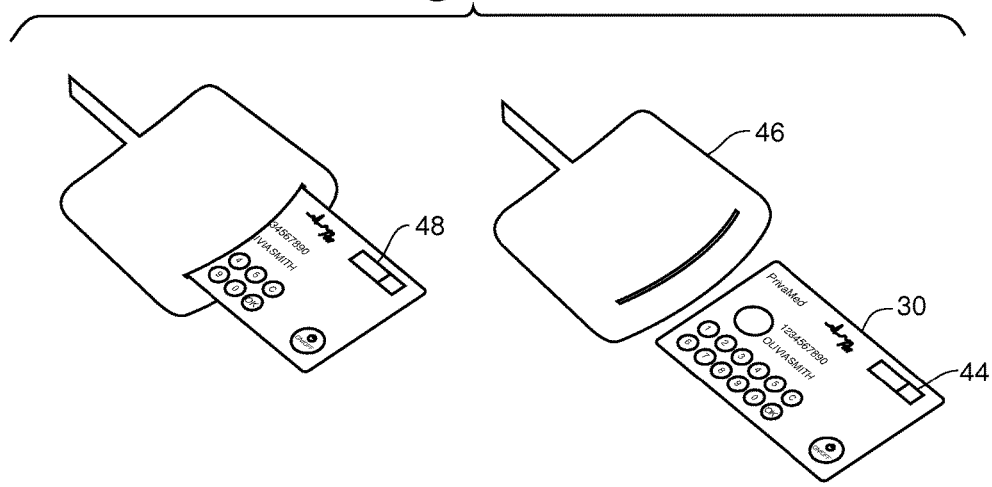
FIG. 4A is a pictorial representation of the embodiment of a user device shown in FIG. 2 inserted into a card reader formed in accordance with the present disclosure.
Figure 4B:
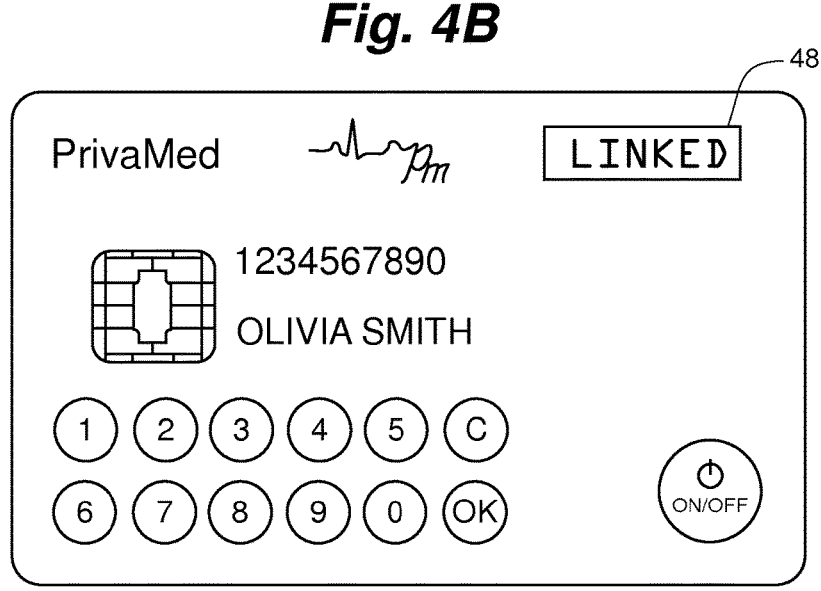
FIG. 4B is a pictorial representation of the embodiment of a user device shown in FIG. 2, shown with the display window that displays another current status of the authentication process, indicating a successful link is established between the user device and a device requesting access thereto.

The aforementioned steps 12, 14, 16 and 18 may all be performed on the first user/patient's device independently of any card or other reader. Referring again to the embodiment shown in FIG. 2, as well as FIG. 4A, once the patient's credentials have been entered, and the gate opens 18 as shown in FIG. 3C by an indicator 44, for example, the user inserts the card 30 in a reader as shown in FIG. 4A. A connection is established between the smart card 30 and the physician's system via insertion of the card in the reader 46, which is connected to the physician's system, for receiving verification of the authenticating credentials from the physician's system.

The access gate remains open for a predetermined period of time during which authenticating credentials submitted by the requesting (second) device 20 must also be received and verified 22. In embodiments, the card also transmits a query with patient information authenticating the patient to the physician's system/second device and a request for the physician/second user to enter the physicians' authenticating credentials. If the timer times out 24 before both the first user and the second user (requester)'s credentials are verified, the handshake fails 26 and the secure data stored in the portable database cannot be accessed. Otherwise, if both the first user and second user credentials are verified within the predetermined time, access is granted to the second device to login to the first user's device to complete an official authentication and to establish a handshake signal with the first device. A communication channel is then opened to permit access 28 to the portable database. The first user device is now linked, the communication channel is open. The card 30 may be updated at this time, or the card 30 may be removed, or disconnected, from the reader 46, in some embodiments, and later updated. In the embodiment of FIGS. 2-4B, for example, card 30 may have an indicator 48 showing that the communication channel is open.

In embodiments, the handshake between the patient's smart card device and the physician's system includes the patient device generating an Answer To Reset (ATR) message when it first connects with the card reader 46 connected to the physician's system, to indicate an electrical reset of the smart card, and that it is open for access. The ATR includes information about the card's state, e.g., that it is open for access, and may include additional information about the communication parameters of the card, and in embodiments, also includes patient data, such as identification data.

In some embodiments, the secure data stored on the portable database is privatized data. In some additional embodiments, the secure data is encrypted with a hierarchical level of access to allow multi-user access to users with different levels and types of access as further described and disclosed in the '146 patent, which is incorporated herein by reference in its entirety. For example, a digital certificate of the device requesting access can be encrypted with the hierarchical level of authorization.

In some embodiments, the patient data that is communicated between the portable database and the physician's system is encrypted before being transmitted, and is then decrypted in accordance with any suitable method known in the art by the receiving device (physician's system or patient device).

Various devices can be used to store the portable database formed in accordance with the present disclosure. Referring to FIG. 2, in various embodiments, the portable database can be stored in a storage device on a display card, or "smart" card 30, which also includes a processing device. The storage device or chip preferably includes a secure storage portion or element for storing data and security tokens, and a non-secure portion for storing encrypted data and encrypted security elements, for example, wherein the processing device accesses the secure data in accordance with methods known in the art. The card 30 also includes a battery and can be powered on or off for use as desired. The card 30 also preferably includes a display 32, and a numeric key pad 34, as well as an internal clock, which may be provided by the processing device. The display card can be any suitable commercially available card formed in accordance with the methods of the present disclosure.

In some embodiments, the display card has internal secure data-storage features that enable a cardholder's PIN to be properly configured and to securely store the cardholder's PIN for authentication in accordance with methods known to those of ordinary skill in the art. The encrypted, secure, data may be stored in the secure storage chip or in other types of memory, including non-secure memory, and accessed using security tokens stored on the chip along with digital keys and certificates in accordance with methods known in the art.

In some additional embodiments, the processing device is configured to verify the cardholder's PIN, and/or the cardholder's biometric authentication or other types of authenticating credentials, when entered by the cardholder in accordance with methods known to those of ordinary skill in the art.

The internal clock and processing device can, in some embodiments, be configured to allow the communications channel between the card and a device requesting access to the portable database on the card to stay open for a predetermined period of time, and to provide a timed "access gate" that opens and stays open only for a given time window, for example, for about 10 seconds to about 30 seconds.

Initial parameters, such as the time window for granting access, can be set by a card issuer when setting up a new user account. In various embodiments, this time window, and, optionally, other parameters, may be changed by the cardholder at a later time.

In embodiments, such parameters, as well as copies of each patient's privatized data, and other information, such as a record of the levels of access granted to various physicians for each patient's data, and issued certificates, keys, and credentials, may also be stored and maintained on a remote server.

Various embodiments of a method formed in accordance with the present disclosure enable a secure communication channel between a portable database including, for example, a patient's encrypted medical records stored on a smart card, such as the display card 30 shown in FIG. 2, and a healthcare provider's or physician's system to enable the physician's system to access and update the patient's records. In one embodiment, with additional reference to FIG. 1 as well as FIG. 3A, the user can submit authenticating credentials at 12 by entering a personal identification number (referred to herein as a PIN) when prompted 40 using the numeric keypad 34.

A keypad in any of the embodiments of the present disclosure may include any device that allows user entry of selected alphanumeric characters into a computer, mobile device, smart card, and the like, including, but not limited to, a touchpad, a keyboard, a keypad, a touchscreen displaying a keyboard and so on.

Figure 3A:
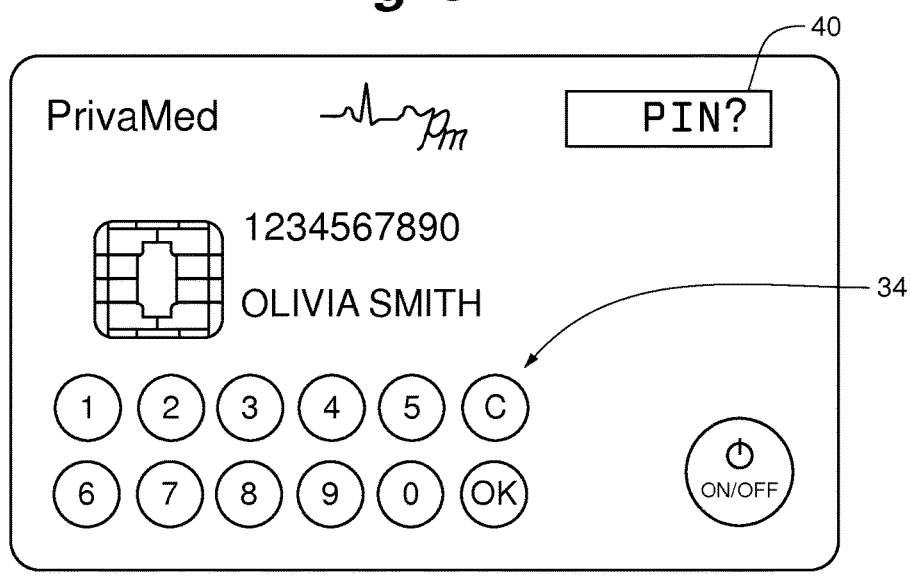
FIG. 3A is a pictorial representation of the embodiment of a user device shown in FIG. 2, shown with a display window that displays a current status of the authentication process.
Figure 3B:
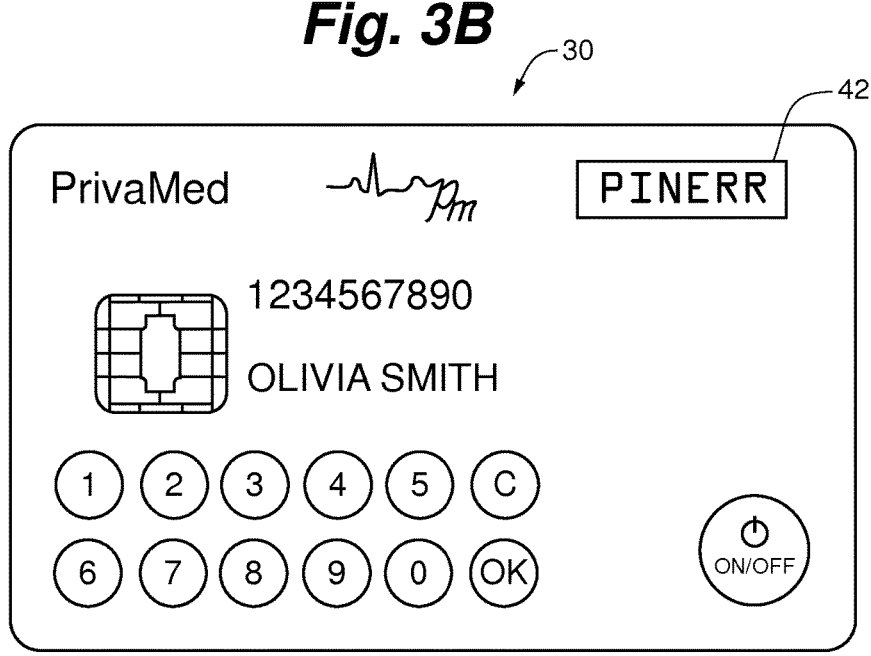
FIG. 3B is a pictorial representation of the embodiment of a user device shown in FIG. 2, shown with the display window that displays another current status of the authentication process.

Referring to FIG. 3B, if the PIN is incorrect, an error message 42 can be shown in the display window 32 on the card 30.

Once the correct PIN number is entered on the card's numeric key pad by the cardholder, the PIN is verified by the card at 14, an access channel is opened at 18 between the card and the physician's system and stays open for a predetermined limited period of time, e.g., 10 seconds. A timer starts concurrently with the opening of the access gate at 16. Referring also to FIG. 3C, the display window 32 on the card, or some other indicator, such as a color of an LED on the card, can change to show this "open" access status 44.

Referring also to FIG. 4A, in some embodiments, once the access gate is open, the cardholder (patient) inserts his or her card 30 into a simple or "dumb" card reader 46, which is operably connected (by cable, or wireless connection, for example) to the physician's computer system. Once the card is inserted in the reader, in some embodiments, a special message is generated by the card and transmitted to the physician's system that includes the patient's ID, which is stored on the card, along with the verification that the patient's credentials (PIN) have been correctly entered and authenticated and requesting entry of the physician's credentials while the access channel is open.

The physician is pre-issued a set of credentials (e.g., a digital key/signature), which can be stored on the physician's computer system, or on a smart card or other smart device, such as a mobile smart phone or tablet, in various embodiments formed in accordance with the present disclosure.

During the predetermined time window, the identifying (ID) credentials issued to the physician's office are used to login to the physician's system at 20. For example, in one embodiment, the physician inserts his/her smart card into a card reader operably connected to the physician's computer system after entering his/her credentials or PIN on the smart card while the access channel is open. In other embodiments, the physician enters his/her PIN into an authentication program running on the physician's computer, using a keyboard or keypad connected to the computer.

If the physician's credentials are verified at 22 before the access gate is timed out at 24, access is granted to the physician's system or device to link to the patient's card and complete an official authentication (handshake) with it. Referring again to FIG. 4A and FIG. 4B, in some embodiments, the successful handshake between the patient's card and the physician's computer system can be indicated by a change in a status indicator on the smart card, such as the display window 32 changing to "LINKED." In other embodiments, a number can be generated in the display window 32 that the physician can use to enter into an authentication program running on his/her computer, or into the physician's smart card inserted into a card reader connected to the physician's computer, that allows access to the patient data at any time during the patient's visit. Once the handshake is successfully completed, secure data can be accessed from and communicated to the patient's card at 28.

In embodiments, once the handshake is established according to the present disclosure, the physician's computer system automatically displays the patient's records on the patient's card to which the physician has been granted access in accordance with an authorization level assigned to the physician. The patient's information on both the patient's card and physician's systems can then be synchronized, and new records produced by the physician during the patient's visit can be downloaded to the patient's card.

In this and other embodiments, privatized data associated with the first user (patient) is stored in a secure database on the user device, such as the smart card 30 shown in FIG. 2, and is encrypted for secure hierarchical multi-user access. The requester (physician, e.g.) accesses the secure data at 28 in accordance with the authorization level assigned to the requester, which may, for example, be encrypted in the requester's authenticating credentials. The credentials including the authorization determine what level the physician has to view, copy, update, and/or create files on the smart card 30.

In some embodiments, the physician's system must periodically re-authenticate itself, at a predetermined fixed time interval, for example, every five (5) minutes, to the smart card 30 in order to be able to continue to access the patient data.

At the end of the patient's visit, after relevant medical data from the visit is written to the patient's card as needed, the card can be removed from the reader and returned to the patient.

In other embodiments, the patient card can be removed once the initial authentication or hand-shake takes place, and re-inserted at the end of the visit to update the patient records stored on the card. In some embodiments, a flag or other indicator is set on the card, and/or a data record is created, once the authentication process and handshake are successfully completed, allowing the physician's system to recognize that the card, when reinserted in the card reader, was previously authenticated to the system, but that the patient's data stored on the patient's smart card or device needs to be updated before the patient leaves. In addition, if a predetermined period of time has lapsed from the time the handshake was completed, for example, after one hour, the patient is prompted to re-enter his/her PIN on his/her card or smart device for verification before the physician system is allowed to access the patient data from the patient's smart card or smart device again.

In other embodiments, once the patient and the physician enter their respective passwords on their respective devices for the first time to complete the authentication process using any of the smart cards or devices formed in accordance with the present disclosure, a key is placed on the patient's device allowing only the currently authorized physician's system (via a physician, receptionist, or other authorized user of the physician system) to access the card again within a predetermined period of time (for example, for 1 hour) without the need for the patient to enter his/her password again. After the predetermined grace period (or after other triggering event, such as a logout command or power off of the user device) the key expires. In some embodiments, if the patient wants to visit a second doctor in the same office within the same grace period as the first doctor, a new key can be generated to handle the second doctor, preferably without logging out the first doctor.

Because the handshake process for authentication is decoupled from the communication channel for communicating (accessing, reading, updating, creating) the secure data, various other smart devices can be easily adapted to the methods of the present disclosure. For example, the smart device for storing the secure database and for enabling a secure connection with a second user's device in accordance with the methods of the present disclosure can be any card or mobile device that includes a processing device, memory, and secure storage, including, without limitation, a smart mobile phone, a tablet, a smart card, and an NFC-enabled device.

In various embodiments, the user device for storing the portable database is a smart mobile device, also referred to herein as a "smart device," for example, a smart phone or tablet.

A smart device for implementing the methods of the present disclosure can include a SIM card secure storage chip for storing both encrypted and unencrypted data, user credentials and security tokens. The smart phone also preferably has a user interface that includes a display and data entry interface, such as a key pad (e.g., real or soft keys).

In various embodiments, the SIM card can be an external card inserted into the smart phone's reader, or an embedded SIM within the hardware of the device. The SIM card can also be any other type known in the art such as, without limitation, an external SIM card inserted into an external reader, or one that can be used in the cloud or as software in the device.

The methods of the present disclosure for storing both encrypted and unencrypted data, user credentials and security tokens can also be implemented using Host Card Emulation (HCE) employed in the cloud, embedded as software within an operating system (OS) of the user's mobile phone, or a combination of the two. Using methods known in the art, for example, HCE can be used to emulate the functions of a SIM card in the cloud, or via embedded software in the OS configured in accordance with the present methods, on a near-field communication enabled device, without relying on access to the physical secure element of the SIM card.

In accordance with some of the embodiments of methods formed in accordance with the present disclosure, the user's PIN or other identifier can be securely stored in the SIM card for use as a reference for authentication of the user's credentials, such as a PIN, which can be input via the mobile smart phone's key pad.

The smart device of the present disclosure includes an internal processor and memory for storing programming steps that when executed by the processor perform the method steps described herein in accordance with the present disclosure.

In addition, the smart phone preferably includes an internal clock that allows a "limited time access" or predetermined period of time for the access channel between the smart phone and the provider system to stay open. The processing device in some embodiments provides the internal clock.

Various embodiments of the methods formed in accordance with the present disclosure using various types of smart devices are described further herein below.

Smart Mobile Device with Bar-Code Generating Programming Application

In some embodiments, a programming application referred to herein as an "app" is downloaded and stored on the smart device, which is configured to create and display a bar code on the smart phone's screen. The bar-code generating app can eliminate the need for an NFC-enabled phone in certain embodiments of the present disclosure.

In one embodiment, a method formed in accordance with the present disclosure for authorizing communication between a smart mobile phone associated with a first user and a second device requesting access to secure data stored on the smart mobile phone includes the first user enabling an app for authenticating the user that prompts the first user to enter a PIN. For authenticating the user's credentials, the user enters the PIN number using the key pad or soft keys on the phone. Referring, for example, to FIG. 1, once the PIN is verified at 14, an authentication code is generated and embedded in a two dimensional barcode that is displayed on the mobile phone's display screen. The barcode also includes the patient's account or ID number, and can include other data, preferably including the time and date the barcode is generated. The generation of the barcode marks the start of the timer at 16 for allowing the access gate to stay open. The barcode's authentication code remains valid for a predetermined period of time, for example, for 10 seconds, after which the barcode image closes, i.e., the access gate times out at 24, and the code becomes invalid or fails at 26.

Within this time window, the physician must scan the barcode generated on the patient's phone using a barcode scanner operably connected to the physician's computer system. The physician must then also enter authenticating credentials, for example, by entering his/her PIN, into a computer programming application running on his/her computer system for linking to the patient's mobile phone. Once both the physician's and patient's credentials are verified, access is granted to communicate data specific to that patient between the portable database on the user's mobile device and the physician's system. The communication channel for transmitting the patient data to and from the mobile device can be enabled using any suitable interface, including, without limitation, Wi-Fi, NFC, cellular networks, and so on.

In one embodiment, the patient's information on the barcode, which includes the patient's authenticating credentials, is sent along with the physicians own credentials to an authentication server. The authentication server authenticates both the physician's and the patient's credentials, and once both parties are verified the authentication server sends a message to the patient's smartphone granting access to the physicians system to access the patient information. Once the authentication is complete, a communications channel is opened between the smart phone and the physician's system or database, such that the patient's information on both systems can be synchronized in accordance with the level of access the physician is authorized.

Smart Mobile Device with NFC

Figure 5:
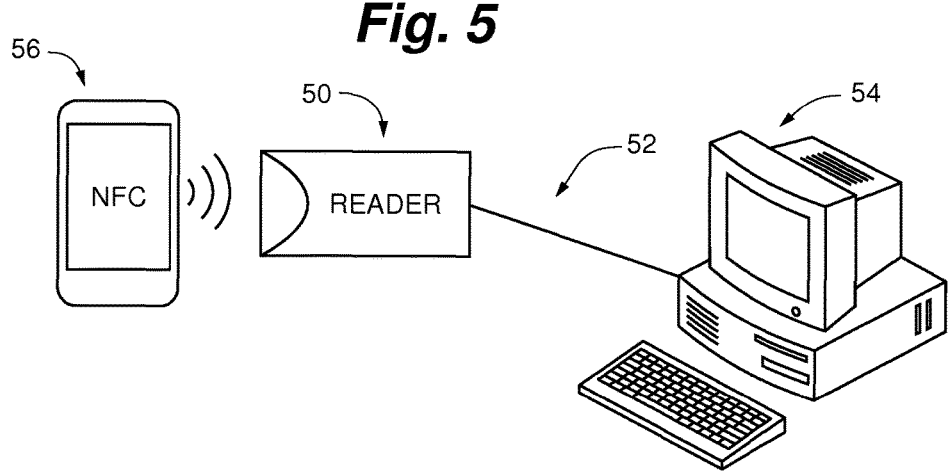
FIG. 5 is a pictorial representation of an embodiment of a system formed in accordance with the present disclosure.

Referring, for example, to FIG. 5, in other embodiments, the user device storing the portable database can be a smart mobile device 56, as described above, which is also NFC enabled, and able to communicate to outside devices using the NFC contactless protocols while emulating a contactless card. In some embodiments, a programming application ("app") is downloaded that allows secure communication with the physician's computer once a handshake signal is established between the mobile device 56 and the physician's computer 54 in accordance with methods formed in accordance with the present disclosure. Preferably, use of the app is PIN protected.

The user's authenticating credentials are installed in a secure storage device on the phone, for example, on the SIM card, and may be stored in the phone's subscriber identity module of the SIM card.

Still referring to FIG. 5, in some embodiments, once the correct PIN number is entered via keys on the user's phone 56, the PIN is verified by the app in the phone against the credentials stored in the phone in accordance with methods known in the art. This will then trigger the limited time open access to stay open for a short period of time. For a connection to be established so that the handshake can be completed, the patient brings his or her smart phone 56 within the necessary proximity of a contactless reader 50, which is operably connected (via cable 52 or wireless connection) to the physician's computer system 54. The reader is capable of reading the NFC/contactless cards and phones (or other appropriate smart devices) with NFC/contactless capabilities.

While still in proximity of the NFC reader, the phone then generates and sends a message requesting the physician to enter his/her PIN. In some embodiments, the message includes: the patient's ID from the card, the verification that the patient has entered his/her correct PIN and that the communications access channel is now established. In some embodiments, the physician can enter credentials using the keyboard operably connected to the physician's computer system. In other embodiments, the PIN can be entered on a smart card, which is then inserted into a card reader operably connected to the system. In other embodiments, the physician (or other authorized user in the physician's office) can enter his/her PIN on an NFC-enabled phone that is read by an NFC reader connected to the physician's computer system. Once the message is received by the doctor's computer system, a response is sent by the physician's system that includes the physician's authenticating credentials. The response is verified by the phone to complete the handshake, and a communications channel is opened between the phone and the provider's system.

Again, the limited time open access allowing the handshake to be established stays open for a limited predetermined period of time, e.g., 10 seconds, to allow an authorized outside entity (physician's computer system) to login to the patient's smart device and access the secure, privatized data stored thereon, through the use of authorized ID credentials. In addition, in preferred embodiments, the privatized data is encrypted for multi-user hierarchical access, such that access to the privatized data is further allowed only in accordance with a level of authorization granted to the physician. This level of authorization can be provided, for example, by embedding a certificate indicating the physician's authorized level of access in the physician's authenticating credentials that are transmitted in the response to the patient's mobile device.

Once the authentication handshake process is completed using a contactless NFC reader, the communication channel for accessing the patient data is open. In some embodiments, the smart device must stay in the proximity of the NFC card reader for the communications channel to stay open for the duration of the conversation between the physician's system and the patient's smart device in order to access the patient's data on the smart device.

In other embodiments, the smart device can be removed from the proximity of the reader once the authentication is completed, and brought back again to the proximity of the NFC reader after the end of the visit for the data on the smart device, e.g., smart phone, to be updated. In this case, a special code is written into the smart phone, or a flag enabled, and/or a data record created, that indicates the smart phone and physician's system have been authenticated. The status of this code or flag is checked when the phone is brought back into contact. If the authentication status is verified (as indicated by the status of the code or flag) the patient's data can be updated, including new files created as needed, on the patient's smart phone.

Display Card with NFC

In other embodiments formed in accordance with the present disclosure, the portable database with the patient's data is stored on a display card that includes an NFC antenna and hardware for contactless interaction with a reader connected to the physician's system. The operation of the NFC Display Card combines the capabilities of the smart display card 30 for PIN entry and verification, and an NFC-enabled phone, interfacing via the NFC reader to the physician's system.

Smart Device with Wireless Connection to Physician's Computing System

Figure 6:
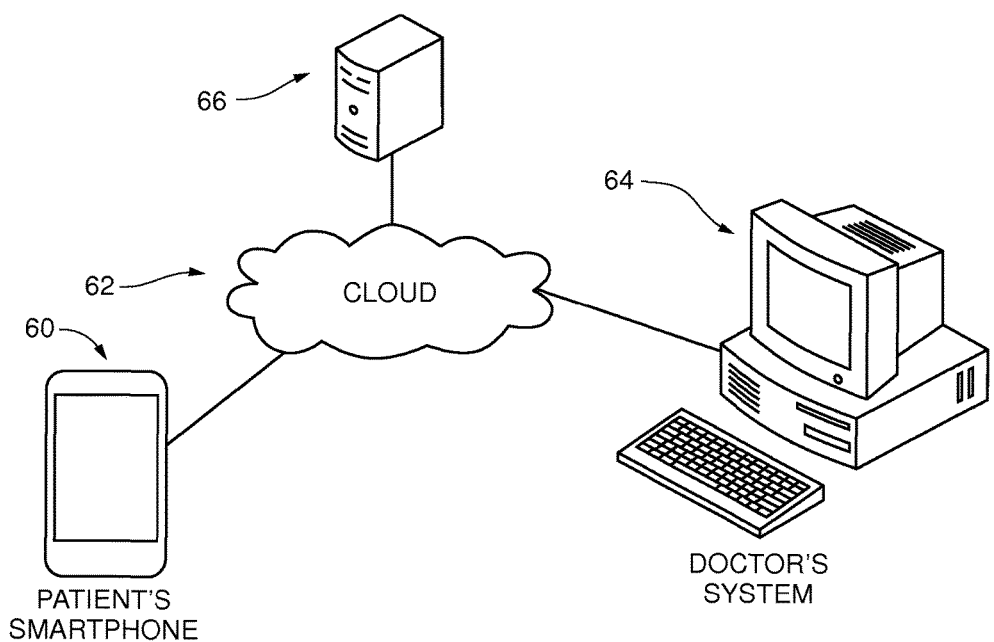
FIG. 6 is a pictorial representation of another embodiment of a system formed in accordance with the present disclosure.

Referring to FIG. 6, in this instance, a user's smart phone 60 uses a wireless cellular or Wi-Fi network 62 to establish a handshake and connect to a physician's system 64 in accordance with the present disclosure. In some embodiments, the cell phone user runs an app for authenticating the user's credentials, as described supra. The user enters his/her PIN on the cell phone via the app. Once the PIN is authenticated, a cryptogram is generated in the phone using a public key, which can include the authentication code, the patient's account number, time and date, and any other relevant identifying information, such as a location code associated with the particular physician. In some embodiments, this cryptogram is then sent to an authentication server 66. The authentication server stores a private key to be able to open the cryptogram and confirm the authentication code. The authentication server ensures that the patient information is correct, and then produces an authorization code, which preferably includes a code and account number of the patient, time and date, and sends it to the physician's system.

Once the PIN is authenticated by the smart phone, the access gate to the smart phone for authentication stays open for a limited period of time, e.g. 10 seconds, during which time the physician's system has time to authenticate its credentials to the patient's smart phone. If the physician's system or device responds within the limited time access with the physician's authenticating credentials, then an access channel is established between the smartphone and physician's system via the authentication server. The physician's credentials (digital key/signature), which are preissued, can be stored on any smart device (phone or card) associated with the physician's system and used to log into the system to be authenticated by the authentication server. Once the physician's office credentials are authenticated, a link is established between the physician's system and the patient's smart phone.

In accordance with various embodiments, the physician's credentials also indicate what level of access the physician is authorized to have to the data on the patient's phone.

In embodiments, establishing a handshake between any type of patient device and the physician's system may include the patient device generating and displaying a code or password upon authentication of the patient credentials. The patient will then allow the physician to view the code or password, which the physician will enter into the physician system, via a physician card, mobile device, or program running on the physician system, to establish the handshake signal between the patient device and the physician's system.

An important feature of embodiments of a smart card formed in accordance with the present disclosure is that the login process of the physician's office for the handshake with the patient's card will be allowed only within the time window that the card is open for communications with the physician's system. This feature of a smart device formed in accordance with the present disclosure, sometimes referred to herein as a "limited time open access," substantially improves the security of the handshake and simplifies usability of the procedure by both the patient and the physician. Advantageously, the limited time open access a) improves security of the entire data access and storage process; b) helps in the prevention of errors, and c) eliminates the need for the use of expensive card-reading terminals.

Updating the Patient's Details on the Patient Device (e.g., Smart Card)

The card details may be changed or the card database searched in various embodiments either directly by the cardholder/patient or by an authorized user, such as an employee of a physician, via, for example, a physician's computer system. Alternatively, a kiosk including a computer may be installed at the physician's office that is configured to allow the cardholder/patient or an authorized user to change and/or view certain details.

In embodiments, the cardholder/patient may change certain settings on a smart card or other user device used to store the patient's privatized data, or allow an authorized user to do so via the physician's system as follows. The cardholder/patient enters a PIN on the card/device. The PIN is verified and the timed access gate is opened. During the time the access gate is open, the card is inserted into a reader attached to the kiosk system or to the physician's office system. If another user device, such as a mobile phone, is used to store the patient's privatized data, it may be scanned or otherwise transmit information to the kiosk or physician's system in accordance with methods of the present disclosure, confirming that the access gate is open. If the cardholder is submitting the change or seeking access to view the database, then the user sees the instruction to enter his/her PIN on the kiosk/computer screen. If an authorized user in the physician's office is submitting the change on the physician's system then the authorized user sees the instruction. The cardholder/patient or authorized user then enters a PIN on the kiosk or physician's computer system's keyboard. If it is the cardholder/patient updating the card details, the PIN entered on the kiosk, for example, may be the same PIN the cardholder/patient enters on the smart card or other user device to open the timed access gate.

Once the second set of credentials are authenticated, a display operably connected to the kiosk or physician's computer shows a menu of actions to be selected by the patient or authorized user. Such actions that may be selected may include, but are not limited to: change timer duration of the access gate; view records of physician visits; view prescriptions; and view other information.

If "change the timer duration" is selected, for example, the current timer duration may be displayed and the user may use arrow keys to increase or decrease the timer value or may enter the time duration in seconds, for example, using the keyboard. The user then saves the selection, exits the menu and withdraws the card from the reader or, if another type of user device such as a mobile phone is used, terminates communication by, for example, exiting an app configured in accordance with embodiments of the present disclosure, or by any other methods known in the art.

In a particular embodiment in which a cellular or mobile phone is the user device, the patient enters his or her PIN on the phone. During the time the access gate is open, the patient brings the phone near a reader/scanner operably connected to the kiosk computer system or the physician's office computer system.

If the patient is performing the search/change, the patient sees the instruction to enter PIN on the kiosk screen. If it is an authorized user in the physician's office system, then the physician/authorized user sees the message. The patient/user enters a PIN (for the patient, it may be the same PIN as he entered on the phone) on the kiosk/physician system's keyboard. Once the second set of credentials are authenticated by the card, a menu of actions to be selected by the user is displayed, as described above. Once any changes are made to certain settings, such as the duration of time that the access gate is open, the user saves the new settings, exits the menu, and exits the app on the phone.

It should be recognized that the system components and smart devices described herein are exemplary only, and that it is contemplated that the methods described herein may be implemented by various combinations of hardware, software, firmware, circuitry, and/or processors and associated memory, for example, as well as other components known to those of ordinary skill in the art.

While the methods and system of the present disclosure have been particularly shown and described with reference to specific embodiments, it should be apparent to those skilled in the art that the foregoing is illustrative only and not limiting, having been presented by way of example only. Various changes in form and detail may be made therein without departing from the spirit and scope of the disclosure. Therefore, numerous other embodiments are contemplated as falling within the scope of the present methods and system as defined by the accompanying claims and equivalents thereto.

What is claimed is:

1. A method for communicating secure, privatized data between a first user device and a second user device, the method comprising:

receiving, by a first user device, authenticating credentials associated with a first user;

verifying, by a first processing device in the first user device, the authenticating credentials received by the first user device;

initiating a timer, by the first processing device, and opening, by the first processing device, an access gate that remains open only for a predetermined period of time in response to the first processing device verifying the authenticating credentials associated with the first user;

generating a verification, by a second processing device associated with a second user device requesting access to secure, privatized data associated with the first user and stored on the first user device, of authenticating credentials associated with a second user accessing the second user device, wherein the authenticating credentials associated with the second user include a key and a digital certificate stored on the second user device, wherein the digital certificate is encrypted with a predetermined authorized level of access granted to the second user device for accessing the secure, privatized data;

receiving, by the first user device, the verification of the authenticating credentials associated with the second user from the second user device after the opening of the access gate and within the predetermined period of time;

granting access, by the first processing device, to the second user device to log in to the first user device to establish a handshake signal in response to the first processing device receiving the verification of the authenticating credentials from the second user device within the predetermined period of time, the second user device logging in to the first user device after being granted access and within the predetermined period of time and thereby establishing a handshake signal with the first user device in response thereto; and opening, by the first processing device, a communication channel between the first user device and the second user device for transmitting the secure, privatized data associated with the first user in accordance with the predetermined level of access and between the first user device and the second user device via the communication channel in response to establishing the handshake signal.

2. The method of claim 1, further comprising establishing a connection between the first user device and the second user device, and receiving, by the first processing device, the verification from the second user device via the connection.

3. The method of claim 2, wherein the first user device is one of a mobile device and a smart card, the method further comprising storing the secure, privatized data in a storage component on the first user device.

4. The method of claim 3, wherein the storage component includes both a secure portion for storing security elements and a non-secure portion for storing encrypted data, including the secure privatized data and encrypted security elements.

5. The method of claim 2, further comprising transmitting information from the first user device to the second user device in response to opening the access gate, the information including a request for the verification of the authenticating credentials associated with the second user from the second user device.

6. The method of claim 5, wherein the privatized data includes patient medical records associated with the first user and stored on the first user device, and the information includes an identifier associated with the patient medical records and a verification of the authenticating credentials associated with the first user.

7. The method of claim 2, wherein the first user device is a mobile device comprising an app installed thereon, the method further comprising receiving and verifying the authenticating credentials associated with the first user and establishing the connection via the app.

8. The method of claim 2, wherein the first user device is a near-field communication enabled device, the connection is a near-field communication connection between the first user device and the second user device, the method further comprising transmitting the information in response to establishing the near-field communication connection between the first user device and the second user device, the first user device being positioned in sufficient proximity to the second user device for establishing the connection.

9. The method of claim 2, further comprising maintaining the communication channel open for a predetermined fixed interval of time in response to establishing the handshake signal, the second user device re-authenticating itself at the predetermined fixed interval via the connection to maintain the communication channel open between the first user device and the second user device for continued access by the second user device to the secure, privatized data.

10. The method of claim 2, further comprising storing the secure, privatized data on the first user device, and, after opening the communication channel, updating the secure, privatized data based on data received from the second user device.

11. The method of claim 2, further comprising placing an indicator on the first user device in response to receiving the verification of the second user device and establishing the connection, interrupting the connection, and then reestablishing the connection and updating the secure, privatized data on the first user device via the communication channel within a preset time interval after interrupting the connection, without requiring re-verification of the second user device, wherein updating further comprises detecting the indicator on the first user device.

12. The method of claim 2, wherein the first user device is a smart card, wherein the connection is established via a smart card reader operably connected to the second user device upon connecting the smart card to the smart card reader within the predetermined period of time, the smart card receiving and verifying the first user's authenticating credentials entered on the smart card by the first user prior to establishing the connection, the method further comprising transmitting the secure, privatized data over the communication channel via the smart card reader.

13. The method of claim 12, wherein the smart card is near-field communication enabled, the smart card reader is a near-field communication device, and the connection is a near-field communication connection.

14. The method of claim 2, wherein the connection between the first user device and the second user device is one of an NFC-enabled connection and a wireless connection.

15. The method of claim 1, wherein the first user device comprises a keypad, the authenticating credentials associated with the first user being received via the keypad.

16. The method of claim 1, further comprising receiving, by the first processing device, a request to view the secure, privatized data in response to opening the access gate, and displaying the secure, privatized data via a graphical user interface operably connected to the first user device.

17. The method of claim 16, further comprising receiving, by the first processing device, a request from the first user device to view and modify settings on the first user device, displaying a menu of allowable actions via a graphical user interface operably connected to the first user device in response to the request, and storing changes while the access gate is open.

18. A method for communicating secure, privatized data between a first user device associated with a first user, and a second user device, the method comprising:
   receiving, by a server, authenticating credentials and an identifier associated with a first user from a first user device;
   verifying, by the server, the authenticating credentials received from the first user device;
   transmitting, by the server, information associated with the first user to a second user device requesting access to secure, privatized data associated with the first user and stored on the first user device, the information including a verification of the authenticating credentials of the first user and a request for verification of authenticating credentials associated with a second user from the second user device, wherein the authenticating credentials associated with the second user include a key and a digital certificate stored on the second user device, wherein the digital certificate is encrypted with a predetermined authorized level of access granted to the second user;
   initiating a timer, by the server, and opening, by the server, an access gate that remains open only for a predetermined period of time in response to verifying the authenticating credentials received from the first user device;
   receiving, by the server, the verification of the authenticating credentials associated with the second user from the second user device only after the opening of the access gate and within the predetermined period of time; and
   opening, by the server, a communication channel for a predefined interval of time for transmitting the secure, privatized data associated with the first user in accordance with the predetermined level of access and between the first user device and the second user device only upon the server receiving verification of the authenticating credentials from the second user device within the predetermined period of time.

19. The method of claim 18, wherein the first user device, the second user device, and the server communicate via a wireless network.

20. The method of claim 18, further comprising receiving, by the server, a request from the first user device to view the secure, privatized data, in response to opening the access gate, and displaying the secure, privatized data via a graphical user interface operably connected to the server.

21. The method of claim 20, further comprising receiving, by the server, a request to view and modify settings on the first user device, displaying a menu of allowable actions via a graphical user interface operably connected to the server in response to the request, and storing changes, by the server, while the access gate is open.

22. A method for communicating secure, privatized data between a first user device associated with a first user, and a second user device, the method comprising:
   receiving, by a server, authenticating credentials associated with a first user from a first user device via an app on the first user device, wherein the first user device is a mobile device;
   verifying, by the server, the authenticating credentials and generating a verification associated with the first user;
   transmitting, by the server, the verification of the first user to the first user device;
   transmitting, by the server, a request for identifying information associated with the first user and a request for verification of authenticating credentials associated with a second user to a second user device requesting access to secure, privatized data associated with the first user and stored on the first user device, wherein the authenticating credentials associated with the second user include a key and a digital certificate stored on the second user device, wherein the digital certificate is encrypted with a predetermined authorized level of access granted to the second user;
   initiating a timer, by the server, and opening, by the server, an access gate that remains open only for a predetermined period of time in response to verifying the authenticating credentials of the first user and transmitting the requests to the second user device;
   receiving, by the server, the verification of authenticating credentials associated with the second user and of the identifying information from the second user device after the opening of the access gate and within the predetermined period of time; and
   opening, by the server, a communication channel for transmitting the secure, privatized data associated with the first user in accordance with the predetermined level of access and between the first user device and the second user device only upon the server receiving the identifying information and the verification of the authenticating credentials from the second user device within the predetermined period of time.

23. The method of claim 22, wherein the identifying information received by the server is derived from a barcode that is scanned by the second user device within a predefined interval of time after being generated, the barcode being generated by the first user device via the app upon receiving the verification from the server, wherein the identifying information includes an identifier associated with the first user and a time and date the identifying information is scanned.

* * * * *